(12) United States Patent
Boehm et al.

(10) Patent No.: US 9,308,098 B2
(45) Date of Patent: Apr. 12, 2016

(54) IMPLANT FOR THE SPINAL COLUMN AND ACTUATING INSTRUMENT

(75) Inventors: Heinrich Boehm, Weimar (DE);
Andreas Burger, Tuttlingen (DE);
Klaus Wenzler, Frittlingen (DE)

(73) Assignee: Heinrich Boehm, Weimar (DE)

( * ) Notice: Subject to any disclaimer, the term of this patent is extended or adjusted under 35 U.S.C. 154(b) by 421 days.

(21) Appl. No.: 13/878,842

(22) PCT Filed: Jul. 25, 2011

(86) PCT No.: PCT/EP2011/062719
§ 371 (c)(1),
(2), (4) Date: Apr. 11, 2013

(87) PCT Pub. No.: WO2012/048920
PCT Pub. Date: Apr. 19, 2012

(65) Prior Publication Data
US 2013/0197648 A1  Aug. 1, 2013

(30) Foreign Application Priority Data
Oct. 11, 2010  (DE) .......................... 10 2010 047 901

(51) Int. Cl.
*A61F 2/44* (2006.01)
*A61F 2/46* (2006.01)
(Continued)

(52) U.S. Cl.
CPC . *A61F 2/442* (2013.01); *A61F 2/44* (2013.01); *A61F 2/447* (2013.01); *A61F 2/4611* (2013.01);
(Continued)

(58) Field of Classification Search
CPC ........ A61B 2/44; A61B 2/4455; A61B 2/447; A61B 2/46; A61B 2/4603; A61B 2/4611
USPC ...................................... 623/17.15
See application file for complete search history.

(56) References Cited

U.S. PATENT DOCUMENTS 6,159,244 A * 12/2000 Suddaby .................... 623/17.11
6,174,334 B1 * 1/2001 Suddaby .................... 623/17.11
(Continued)

FOREIGN PATENT DOCUMENTS

DE   20207853 U1   10/2002
DE   19604246 B4   6/2006
(Continued)

*Primary Examiner* — Christian Sevilla
*Assistant Examiner* — Eric S Gibson
(74) *Attorney, Agent, or Firm* — Kriegsman & Kriegsman

(57) ABSTRACT

The invention relates to an implant device, comprising an actuating instrument (110) and a height-adjustable implant (10) having a substantially U-shaped inner basket (11) and a U-shaped outer basket (60), wherein the inner basket (11) of the implant (10) is embraced by the outer basket (60) and telescopically guided, and the inner basket (11) and outer basket (60) are equally aligned, and wherein the limb (12, 13) of the inner basket (11) and the limb (61, 62) of the outer basket (60) are aligned so that a substantially continuous lateral opening (80) results, and the inner (11) and outer (60) baskets can be fixed with respect to each other in a predetermined end position, and wherein vertebral support surfaces are provided on the end faces (18, 63) of the baskets (11, 60), wherein the actuating instrument (110) has a fixation rod (111) and an expansion mechanism with sliding elements (122), and the inner basket (11) and fixation rod (111) have corresponding elements (26, 112), by means of which a detachable, rigid connection between the fixation rod (111) and inner basket (11) is achieved, and wherein by actuating the expansion mechanism on the actuating instrument, the outer basket (60) can be moved in the longitudinal direction (L) by the engagement of the sliding elements (122) at the limbs (61, 62) opposite the inner basket (61).

23 Claims, 18 Drawing Sheets

Figure 1:
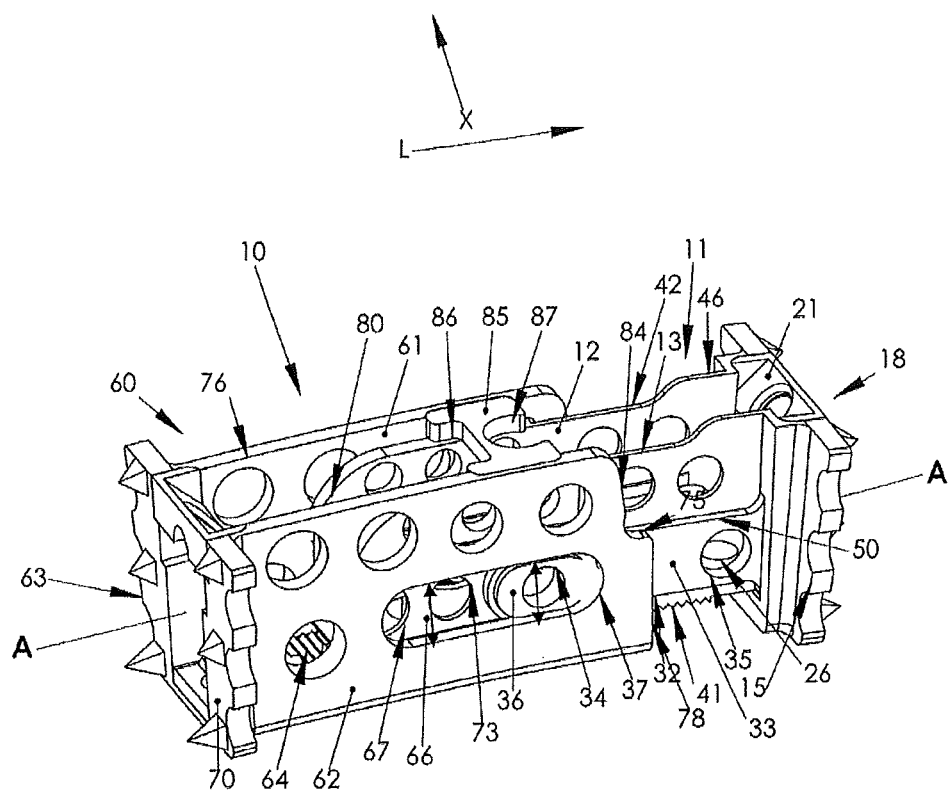

(51) Int. Cl.
    *A61F 2/28*                (2006.01)
    *A61F 2/30*                (2006.01)

(52) U.S. Cl.
    CPC ....... *A61F 2/4637* (2013.01); *A61F 2002/2835* (2013.01); *A61F 2002/3052* (2013.01); *A61F 2002/30153* (2013.01); *A61F 2002/30484* (2013.01); *A61F 2002/30509* (2013.01); *A61F 2002/30522* (2013.01); *A61F 2002/30551* (2013.01); *A61F 2002/30579* (2013.01); *A61F 2002/30596* (2013.01); *A61F 2002/30616* (2013.01); *A61F 2002/30785* (2013.01); *A61F 2002/30843* (2013.01); *A61F 2002/30904* (2013.01); *A61F 2002/4475* (2013.01); *A61F 2002/4624* (2013.01); *A61F 2002/4635* (2013.01); *A61F 2002/4642* (2013.01); *A61F 2220/0025* (2013.01); *A61F 2250/0007* (2013.01)

(56) References Cited

U.S. PATENT DOCUMENTS

| | | | |
|---|---|---|---|
| 6,200,348 B1* | 3/2001 | Biedermann et al. | 623/17.11 |
| 6,332,895 B1* | 12/2001 | Suddaby | 623/17.11 |
| 6,419,705 B1* | 7/2002 | Erickson | 623/17.16 |
| 6,562,074 B2 | 5/2003 | Gerbec et al. | |
| 8,241,363 B2* | 8/2012 | Sommerich et al. | 623/17.16 |
| 8,282,683 B2* | 10/2012 | McLaughlin et al. | 623/17.11 |
| 8,353,961 B2* | 1/2013 | McClintock et al. | 623/17.15 |
| 8,425,608 B2* | 4/2013 | Dewey et al. | 623/17.16 |
| 8,591,587 B2* | 11/2013 | Refai et al. | 623/17.15 |
| 8,715,351 B1* | 5/2014 | Pinto | 623/17.15 |
| 8,828,019 B1* | 9/2014 | Raymond et al. | 606/99 |
| 2003/0074064 A1* | 4/2003 | Gerbec et al. | 623/16.11 |
| 2004/0049271 A1* | 3/2004 | Biedermann et al. | 623/17.11 |
| 2004/0162618 A1* | 8/2004 | Mujwid et al. | 623/17.15 |
| 2005/0080422 A1* | 4/2005 | Otte et al. | 606/85 |
| 2006/0074431 A1* | 4/2006 | Sutton et al. | 606/90 |
| 2006/0200244 A1* | 9/2006 | Assaker | 623/17.15 |
| 2006/0287725 A1* | 12/2006 | Miller | 623/17.11 |
| 2007/0123987 A1* | 5/2007 | Bernstein | 623/17.11 |
| 2007/0255409 A1* | 11/2007 | Dickson et al. | 623/17.11 |
| 2007/0255410 A1* | 11/2007 | Dickson et al. | 623/17.11 |
| 2008/0039948 A1* | 2/2008 | Biedermann et al. | 623/17.16 |
| 2008/0114467 A1* | 5/2008 | Capote et al. | 623/23.47 |
| 2009/0164018 A1* | 6/2009 | Sommerich et al. | 623/17.16 |
| 2010/0179594 A1* | 7/2010 | Theofilos et al. | 606/247 |
| 2010/0280616 A1* | 11/2010 | Frasier | 623/17.16 |
| 2011/0202135 A1* | 8/2011 | Baek et al. | 623/17.16 |
| 2011/0208306 A1* | 8/2011 | Farris | 623/17.11 |
| 2011/0218628 A1* | 9/2011 | Ciupik et al. | 623/17.11 |
| 2011/0218631 A1* | 9/2011 | Woodburn et al. | 623/17.16 |
| 2011/0257750 A1* | 10/2011 | Barrall | 623/17.16 |
| 2012/0226356 A1* | 9/2012 | Hirschl | 623/17.16 |
| 2012/0330422 A1* | 12/2012 | Weiman | 623/17.16 |
| 2013/0006359 A1* | 1/2013 | Fedorov et al. | 623/17.16 |
| 2013/0085572 A1* | 4/2013 | Glerum et al. | 623/17.16 |
| 2013/0197648 A1* | 8/2013 | Boehm et al. | 623/17.16 |
| 2014/0172104 A1* | 6/2014 | Dugal et al. | 623/17.16 |
| 2014/0188225 A1* | 7/2014 | Dmuschewsky | 623/17.16 |
| 2014/0243982 A1* | 8/2014 | Miller | 623/17.16 |
| 2014/0257484 A1* | 9/2014 | Flower et al. | 623/17.15 |
| 2014/0257486 A1* | 9/2014 | Alheidt | 623/17.15 |
| 2014/0277470 A1* | 9/2014 | Baynham | 623/17.13 |
| 2014/0277473 A1* | 9/2014 | Perrow | 623/17.15 |
| 2014/0277493 A1* | 9/2014 | Glad et al. | 623/17.16 |
| 2014/0277501 A1* | 9/2014 | Northcutt et al. | 623/17.16 |
| 2014/0277509 A1* | 9/2014 | Robinson et al. | 623/17.16 |
| 2014/0296983 A1* | 10/2014 | Fauth et al. | 623/17.16 |
| 2014/0343678 A1* | 11/2014 | Suddaby et al. | 623/17.16 |
| 2015/0012097 A1* | 1/2015 | Ibarra et al. | 623/17.15 |
| 2015/0012098 A1* | 1/2015 | Eastlack et al. | 623/17.15 |
| 2015/0018954 A1* | 1/2015 | Loebl et al. | 623/17.16 |
| 2015/0057755 A1* | 2/2015 | Suddaby et al. | 623/17.16 |
| 2015/0094814 A1* | 4/2015 | Emerick et al. | 623/17.16 |

FOREIGN PATENT DOCUMENTS

| | | |
|---|---|---|
| DE | 102008010607 A1 | 8/2009 |
| EP | 1267755 B1 | 5/2006 |
| EP | 1878408 A1 | 1/2008 |
| FR | 2850563 A1 | 8/2004 |
| WO | 03032812 A2 | 4/2003 |

\* cited by examiner

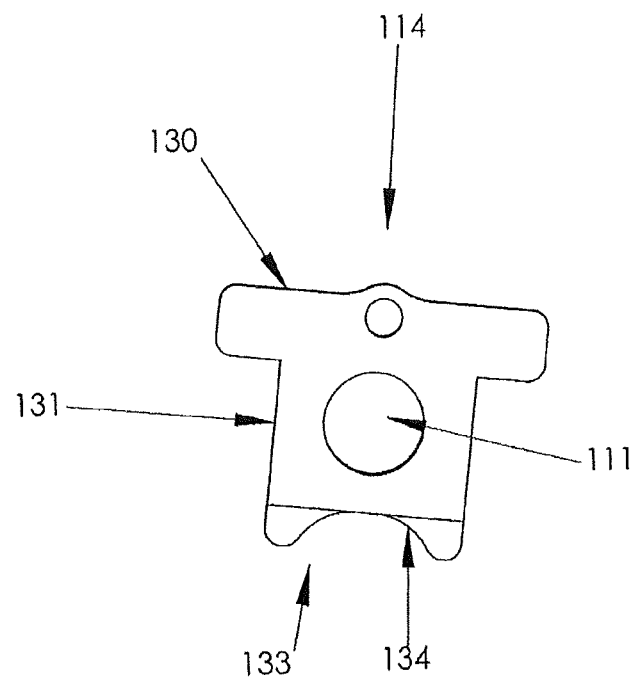
Fig.: 14

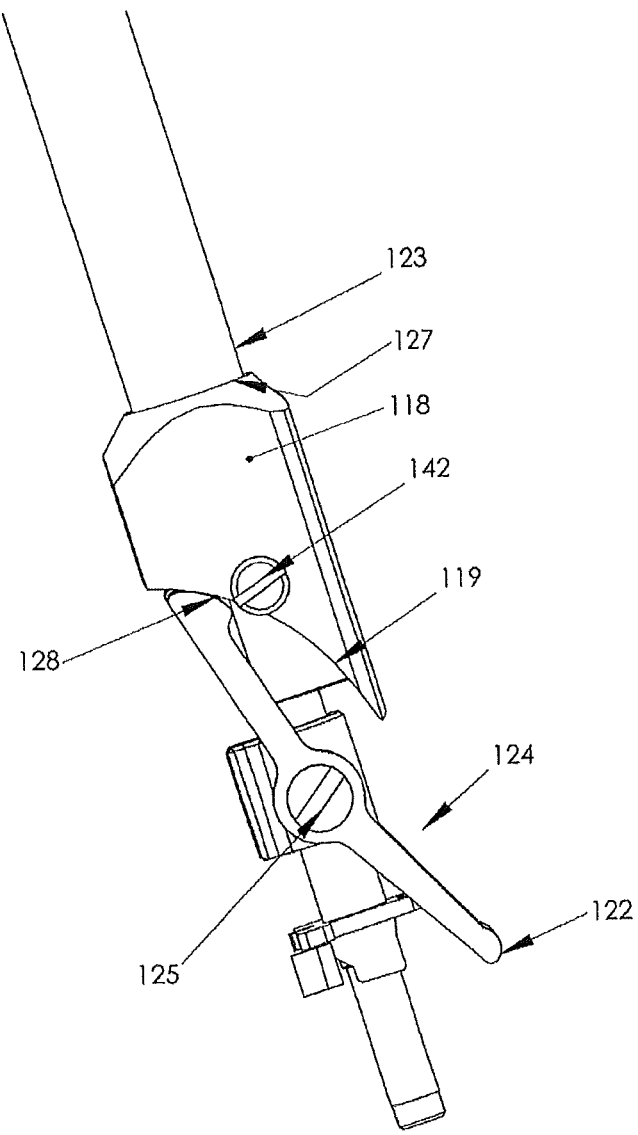
Fig.: 15

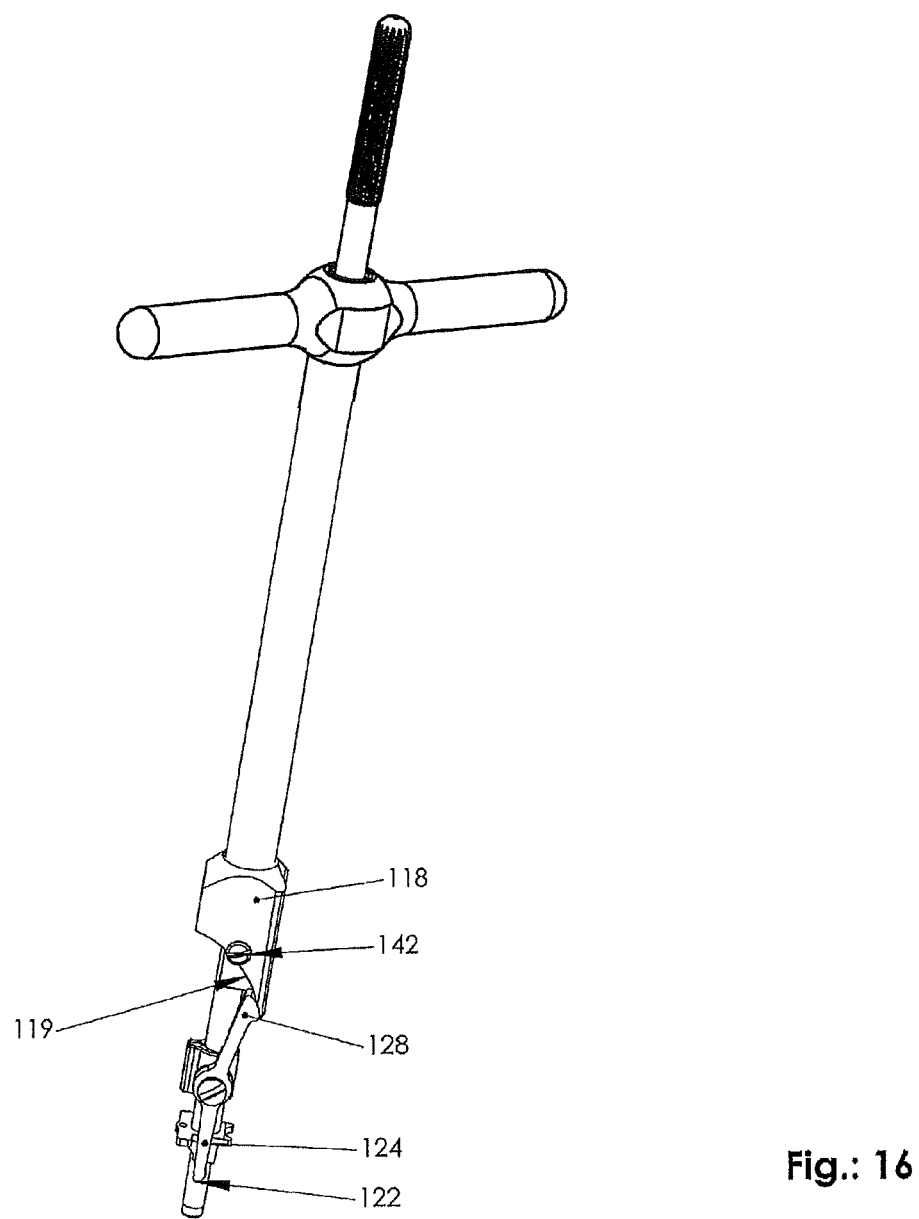
Fig.: 16

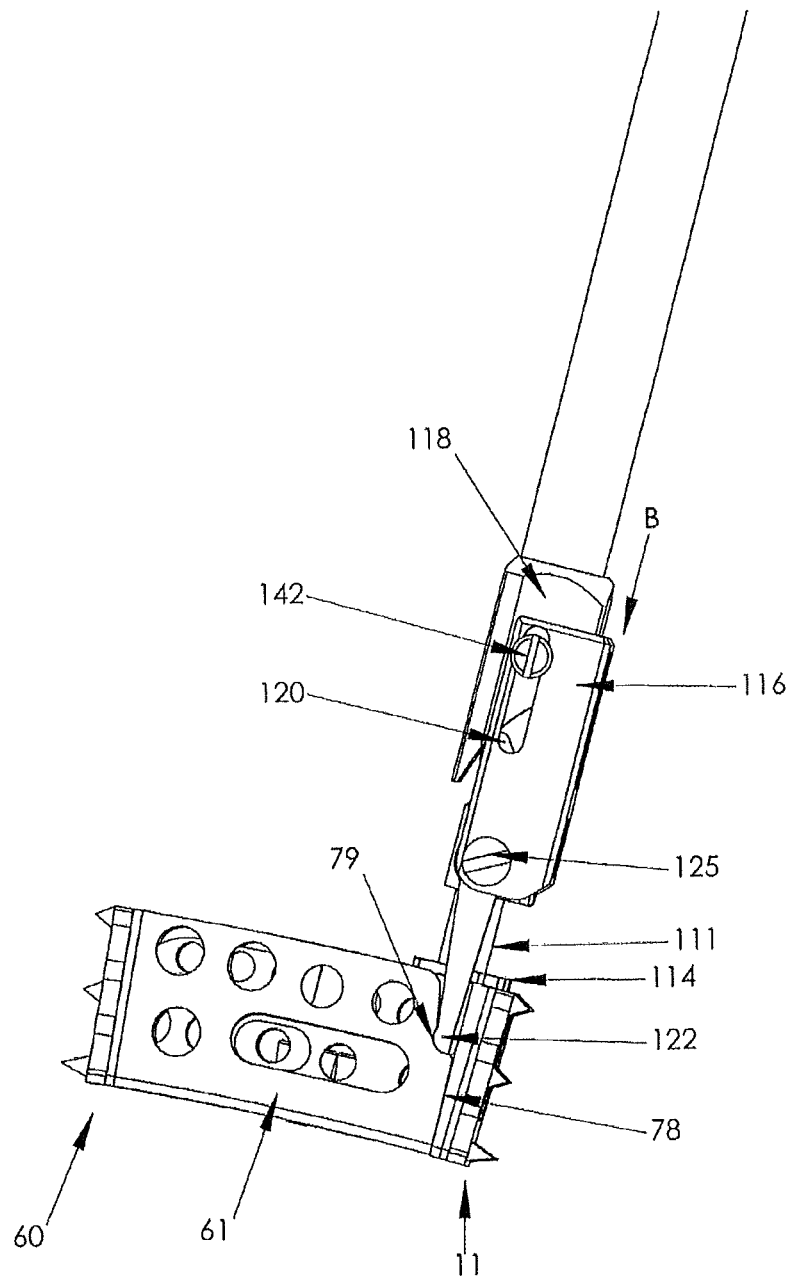
Fig.: 17

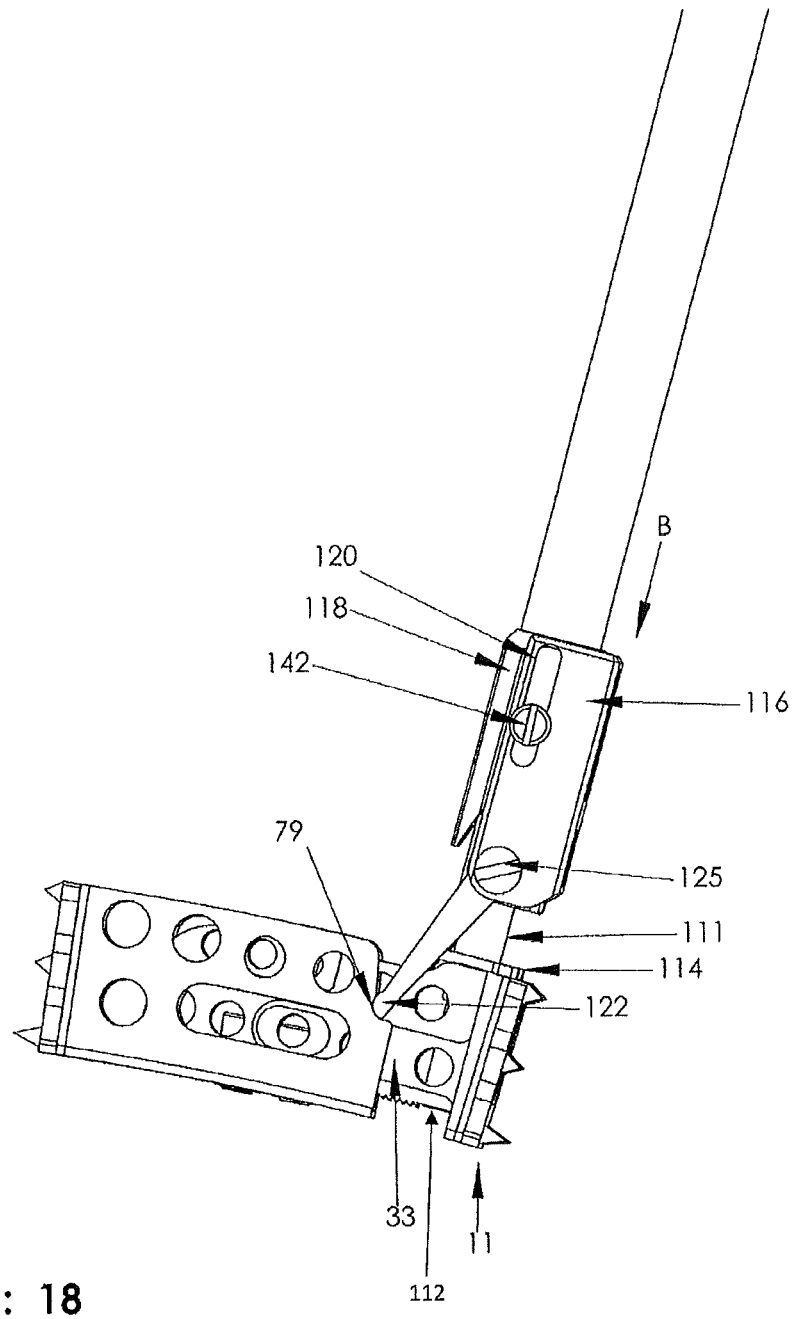
Fig.: 18

IMPLANT FOR THE SPINAL COLUMN AND ACTUATING INSTRUMENT

The present invention relates to an implant device comprising a height-adjustable implant for the spinal column, for the reconstruction of spinal column defects, and an actuating instrument. In particular, the implant is used to replace parts of the vertebral bodies and adjoining intervertebral disks.

The previously known corpectomy implants are based on the principle of a jack and thus permit height adjustability. However, a disadvantage of these implants is that scarecely any growth of bone through the implants is possible, since they have a sleeve-shaped configuration and thus permit little or no contact with the healthy bone and also provide little biological stimulation to formation of new bone. Moreover, after the wound has healed, the entire load in these cases bears on the implant, which can lead to fatigue fractures of the cover plates of the anchoring vertebrae, with the implant giving way, and to painful malpositioning, or even the danger of paraplegia by compression of the spinal cord.

Height-adjustable implants with this kind of sleeve-shaped configuration are known from DE 196 04 246 B4 and from DE 202 07 853 U1.

A further disadvantage of these implants is that the change in the height of the implant can only take place in a linear manner, i.e. the implant does not allow the option of following the natural slight curvature or lordosis, for example in the cervical region.

A further disadvantage of the previously known implants is that, because of their design, they cannot safeguard the spinal canal against renewed narrowing, for example by inadvertent shifting of bone chips past the implant or, alternately, introduced bone cement.

Another disadvantage of these implants following the principle of a jack is that they give way, particularly if no additional osseous stiffening is provided.

U.S. Pat. No. 6,562,074 B2 discloses a rectangular, height-adjustable implant composed of an outer cage and inner cage and of a reinforcing element. Because of this reinforcing element, this implant does not allow any bone to grow through. In this device, the outer cage and inner cage are aligned with each other in such a way that the bottoms of each of the U-shaped outer and inner cages form the vertebral support surfaces.

Corpectomy implants are also known that have the shape of a U-shaped cage. These implants can be filled with bone substance, such that an ossification of the implant can be achieved. These implants do not provide any height adjustability as such. In these implants, the adaptation of the implants to the required height takes place in such a way that they are shortened to the desired length during the operation and the outer edges are then rounded slightly. A disadvantage of these implants is that they subside into the vertebral bodies, which can lead to malpositioning and renewed narrowing of nerve structures/spinal cord or to deterioration/failure of the adjacent intervertebral disks.

A further disadvantage of these implants is that length determination is often difficult, and shortening is not carried out to the appropriate length, with the result that the implant has to be removed again and another implant implanted.

Moreover, EP 1 267 755 B1 discloses a height-adjustable vertebral body implant composed of a first, substantially U-shaped or C-shaped cage and of vertebral support surfaces configured on the cage. The first cage is an inner cage which is embraced by a second, outer U-shaped or C-shaped cage and is guided telescopically, wherein both U-shaped cages are equally aligned and the implant formed from the two cages is likewise U-shaped. The limbs of the inner and outer cages are aligned in such a way as to form a continuous opening that lies opposite the bottoms of the cages. Vertebral support surfaces are provided on the front faces of the cages. In the area connecting the limbs, the inner cage also has an oblong hole that extends in the longitudinal direction and has a toothing on one side. The two cages are moved relative to each other by means of an actuating instrument with an outer toothing. When the desired height is reached, the cages are secured in the respective position by three screws.

The implant is adjustable in height and can be filled with bone substance, through the continuous opening, and can thereby undergo bone incorporation. Moreover, the implant subsides only slightly into the verterbral body.

The two cages are fixed with screws in the direction of the spinal cord. As a result of the wall reinforcements of the outer cage in the area of the fixation screws, the side facing the spinal cord/dura also has a forward bulge, which can either cause local irritation of the dura or means that a positioning at a greater distance from the spinal cord is optimal.

A further disadvantage of this implant is that, when only one vertebral body is used, as is often the case, e.g. in the cervical region, the design of the implant means that it provides too little expansion and, as a consequence, cannot be reliably anchored.

Moreover, for use in the upper region of the thoracic spine, the disproportion between expansibility and required expansion in this implant often proves to be an exclusion criterion for use in the transthoracic (ventral) technique.

For the surgical option of dorso-lateral implantation (from the back, past the side of the spinal cord), there is also the difficulty, in addition to poor expansibility, that the expansion mechanism cannot be used "round the corner" with the implant turned through 90 degrees.

A further disadvantage of the known implant is the high radiation burden to which the patient is exposed during the implantation.

This implant is also unsuitable as a cervical implant, because of the large amount of space required by the displacement and fixation mechanism and because of the resulting large overall size.

DE 10 2008 010 607 teaches a height-adjustable vertebral body implant with a U-shaped outer cage, and a U-shaped inner cage in lordotic form guided in the outer cage. The implant is U-shaped. Fixing is achieved by interlocking of the corresponding teeth arranged on the two cages. Prior to the interlocking, the toothing provided on the inner cage points slightly in the direction of the interior of the cage, such that the inner cage is movable relative to the outer cage. When the desired position is reached, the teeth provided on the inner cage are pressed slightly outward against the teeth of the outer cage by means of a blocking element, and a self-locking fit is thereby obtained.

In this implant, the expansion direction is not limited to the implantation direction. Moreover, irritation of the dura is avoided, and, as a result of the lordotic shape, no additional implants are required. Moreover, this implant is also suitable for the cervical region.

However, a disadvantage of this implant is that difficulties arise from the expansion of the two cages, i.e. the movement of the two cages relative to each other, and from an adjustment of the two cages along the slight line of curvature corresponding to the lordotic shape. Moreover, once the inner cage and outer cage have been interlocked, it is very difficult to reverse an overexpanded position and bring the inner cage back again to the "displacement position" relative to the outer cage.

The object of the present invention is to make available height-adjustable implants which can be filled with bone or bone replacement substance, which can be used as a corpectomy cage, in which the direction of expansion does not depend on the direction of implantation, which are easier to operate, and in which an overexpansion can later be easily reversed, and also an actuating instrument therefor.

This object is achieved by the features of claim 1.

According to the invention, the actuating instrument comprises a fixation rod and an expansion mechanism for actuation of sliding elements, and the inner cage of the implant and the fixation rod have corresponding elements of a releasable connection element, such that the fixation rod can be rigidly connected to the inner cage. By actuating the expansion mechanism, the outer cage can be moved relative to the inner cage in the longitudinal direction (L direction) by the sliding elements, wherein the engagement of the sliding elements on the outer cage takes place on the limbs. The sliding elements preferably engage on the side of the limbs located opposite the front face of the outer cage, such that only a slight expansion movement is needed, and the view and the operation are not obstructed by bulky instruments obstructing the view.

As the connection element of the inner cage, a threaded bore is preferably provided on the bottom of the inner cage and serves to receive a corresponding outer thread on the fixation rod of the actuating instrument, that is to say the corresponding connection element. When the fixation rod is screwed with its outer thread into the bore in the bottom of the inner cage, a rigid connection between fixation rod and inner cage is obtained.

However, since the actuating instrument in addition also has an expansion mechanism with sliding elements, the actuation of the expansion mechanism causes a movement of the sliding elements, in particular lever ends, in the longitudinal direction (L direction) relative to the fixation rod with inner cage and, consequently, a movement of the outer cage relative to the inner cage.

By releasing the expansion mechanism, it is possible to move the sliding elements back in the L direction and, in this way, cancel an overexpansion between outer cage and inner cage.

In order to ensure an expansion movement of the two cages that follows the lordotic shape, the outsides of the limbs of the inner cage preferably have a support surface which extends in the longitudinal direction and on which the sliding elements, which can be lever ends for example, bear during the actuation of the expansion mechanism. Good guiding is achieved by this feature.

A further improvement in the guiding of the two cages during the expansion movement can be achieved by the fact that, on the side of the limbs that lies opposite the front face of the outer cage, a step is provided which serves to support the sliding elements of the actuating instrument.

In order to facilitate the positioning of further instruments, for example hexagon wrenches or retainers, in the lateral opening of the implant and to prevent slipping of the operating instruments, the outer cage of the implant preferably has a bridging web which bridges the lateral opening and which is rigidly connected to the limbs of the outer cage and comprises recesses for receiving instruments.

The bridging web covers only a small area of the opening, so as to obstruct the view during implantation as little as possible.

There is no need for additional implants, since the implant according to the invention has a line of slight curvature corresponding to the lordotic shape. In order to obtain the movement of the two cages relative to each other along the line of lordotic curvature and to prevent jamming, the cages, preferably the limbs thereof, are provided with elements which correspond to one another and which serve to guide the expansion movement in a movement that follows the lordotic shape. These guide elements can be designed as corresponding support surfaces in the outer cage and inner cage, but also by openings, in particular oblong holes following the lordotic shape, with projections guided into these openings. Other corresponding guide means are also possible, as long as they permit guiding along the lordotic shape. Like the bridging web, the projections guided in the openings also serve to prevent the inner cage falling out of the outer cage perpendicularly with respect to the longitudinal direction.

When the desired end position in the displacement direction is reached, the inner cage is fixed relative to the outer cage. The fixing can be achieved in various ways, preferably by screwing. In a particularly preferred embodiment, the bottom of the inner cage has an oblong hole, and the bottom of the outer cage has various openings that serve for screwing.

In order to avoid fatigue fractures in the cover plates of the anchoring vertebrae, the implant according to the invention preferably has several openings in the limbs, in the bottom and in the vertebral support surfaces, which openings serve to provide better through-growth of bone.

The actuating instrument comprises a fixation rod and an expansion mechanism, wherein, in a preferred embodiment, the outer thread that serves for screwing into the bores on the bottom of the inner cage is provided at the end of the fixation rod.

In order to achieve a good force transmission, to avoid jamming and to keep the size of the actuating instrument as small as possible, the actuating instrument has the sliding elements and the expansion mechanism preferably at the end of the fixation rod.

The expansion mechanism should be displaceable relative to the fixation rod, in order to permit the actuation of the expansion mechanism and, therefore, a pivoting movement of the actuating elements or the displacement movement of the sliding elements relative to the fixation rod.

In a preferred variant, the expansion mechanism comprises a force transmission element with an oblique pressing surface on the underside. The lever elements, which comprise the sliding elements, are mounted pivotably about an axis. The pivot axis is situated near the end of the rod, such that the pivoting movement is very small, especially since the ends of the sliding elements end above the end of the fixation rod. Astonishingly, this small pivoting movement of the sliding element permits the displacement of the cages. In the rest state, the upper end of the lever elements bears on the pressing surface such that, when force is introduced by the oblique pressing surface of the force transmission element, the lower end of the lever element, i.e. the displacement element, can be pivoted out of the rest position.

The force transmission element is surrounded by a U-shaped housing, and the housing has an oblong hole, which extends along the axis of the fixation rod and in which is guided a rod that passes through the oblong hole and force transmission element.

The lower end of the housing is crossed by an axis on which the lever elements are secured pivotably.

The actuation of the expansion mechanism takes place with a force acting downwardly along the fixation rod. Preferably, the fixation rod has a threaded spindle, onto the outer thread of which an actuating sleeve can be screwed. By the screwing movement, the lower edge of the actuating sleeve presses the force transmission means in the direction of the rod end and thereby actuates the expansion mechanism.

By means of the threaded spindle, it is possible to achieve an exact metering of the force acting on the force transmission element.

In the expansion mechanism according to the invention, provision is also made that the fixation rod has a positioning disk which is mounted so as to be rotatable near the rod end but not displaceable, and that the displacement path of the expansion mechanism along the fixation rod is limited by the positioning disk and the threaded spindle, and the expansion mechanism, together with the positioning disk, is rotatable relative to the fixation rod, but the expansion mechanism is not rotatable relative to the fixation disk.

Preferably, the implant device according to the invention additionally has a retainer for taking up the torque acting on the implant, which can be positioned in the recess in the bridging web.

A particular feature of the invention is also that the implant can first of all be optimally positioned, and then the surfaces of the anchor vertebrae that are not needed for the support can be trimmed. This avoids weakening the implant bearing by trimming the end plates prior to implantation, as is structurally necessary in the implants known from the prior art. Optimal trimming of the adjacent vertebrae results in rapid incorporation of the implant and fewer possibilities of complications (subsidence, delayed ingrowth or lack of ingrowth).

A further advantage of the present invention is that the expansion mechanism can also be used "round the corner" with an implant turned through 90 degrees, since the openings for engagement of the instruments are arranged laterally and, in the implant according to the invention, no fixing has to take place at the bottom.

The present invention is also characterized in that the implant is implanted with an implantation instrument and the implantation instrument does not interfere with the X-ray monitoring.

The invention is described in more detail below on the basis of illustrative embodiments.

Figure 2:
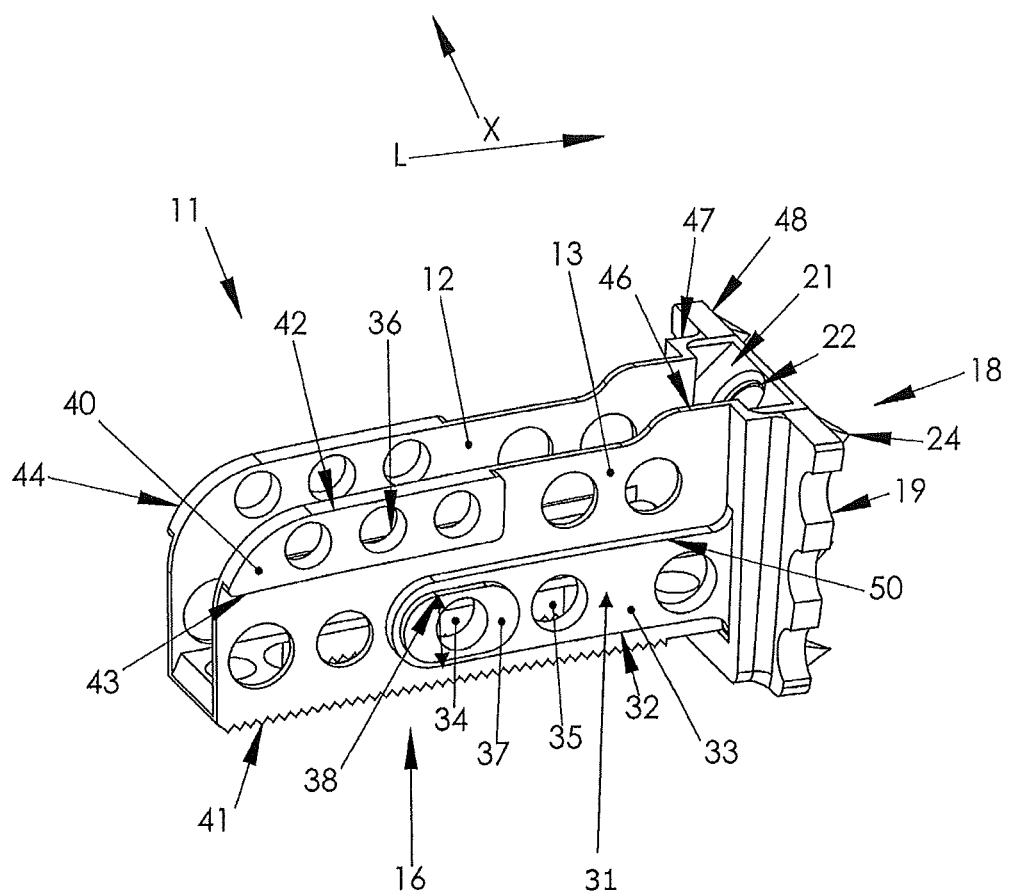
Figure 3:
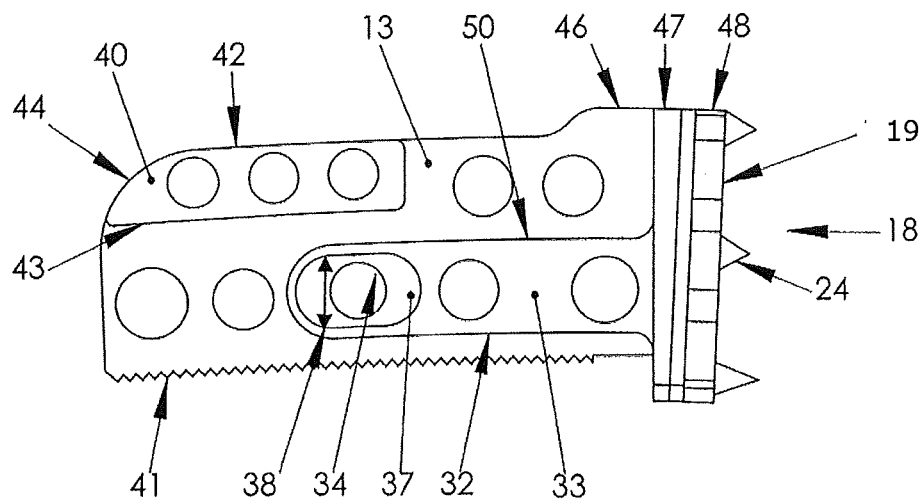
Figure 4:
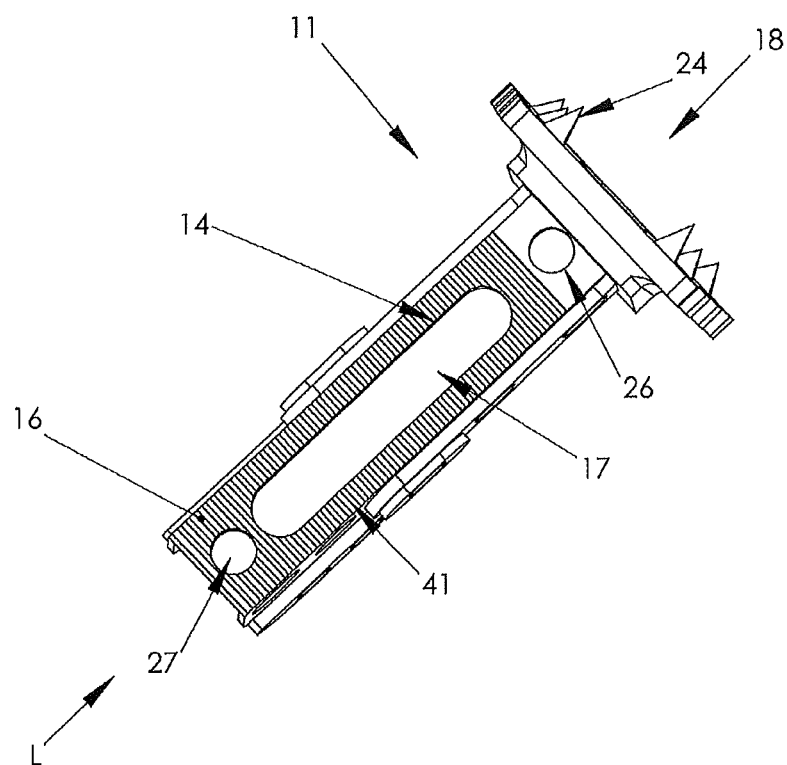
Figure 5:
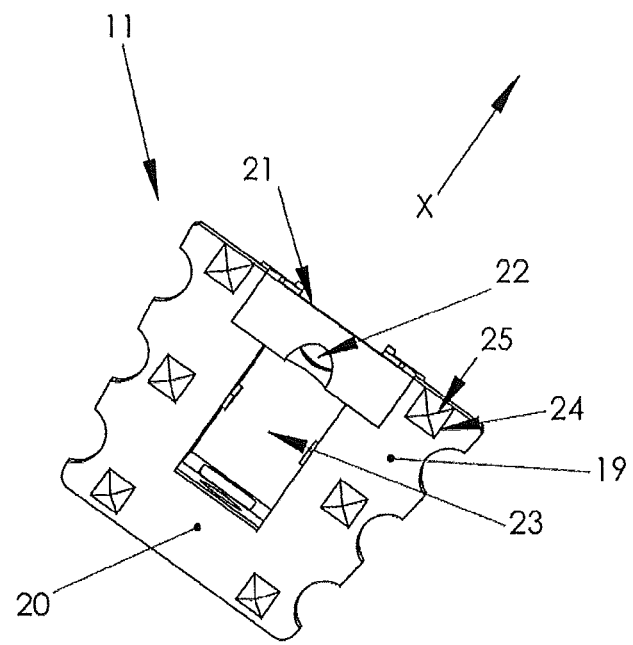
Figure 6:
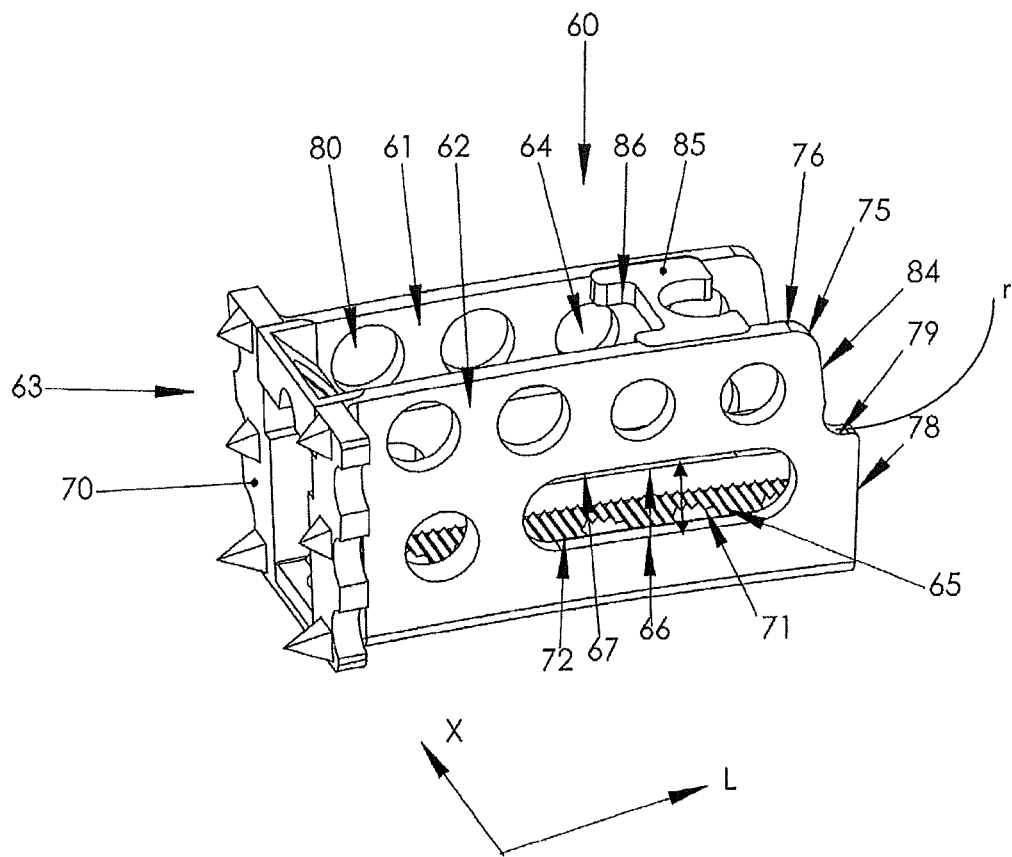
Figure 7:
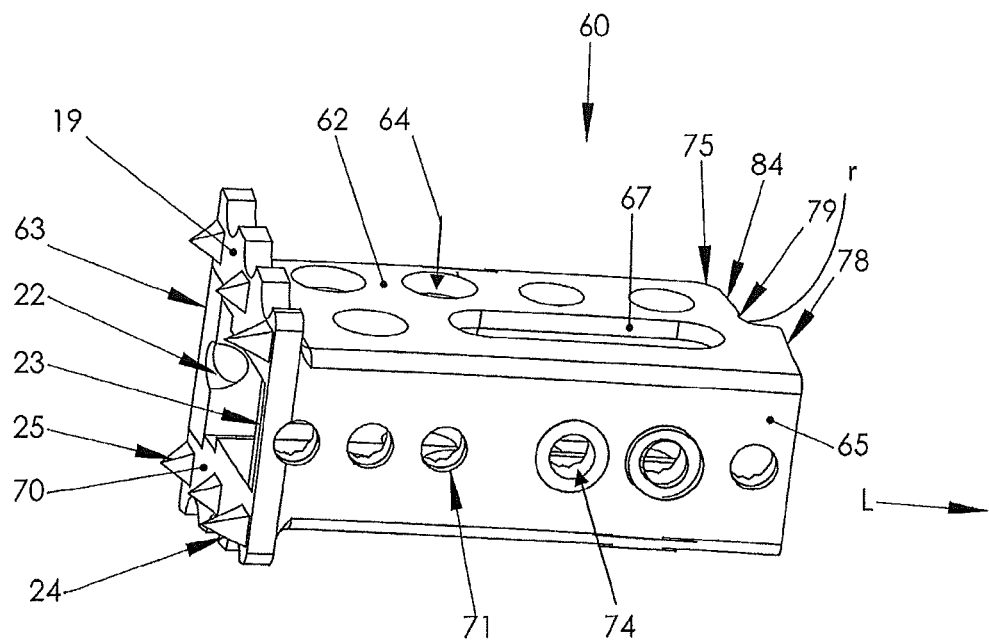
Figure 8:
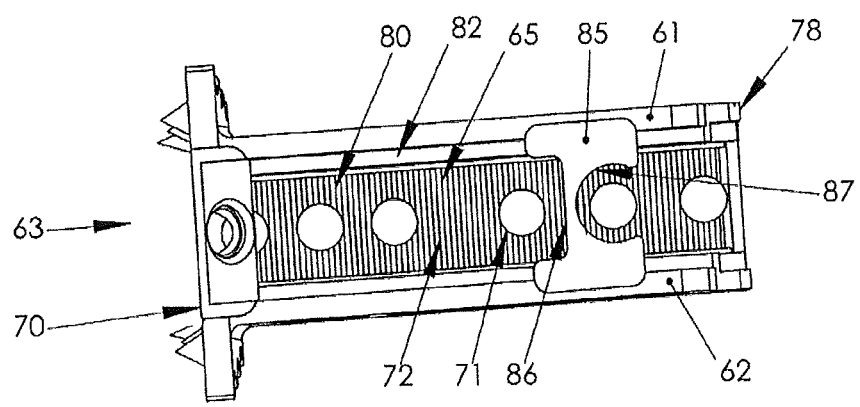
Figure 9:
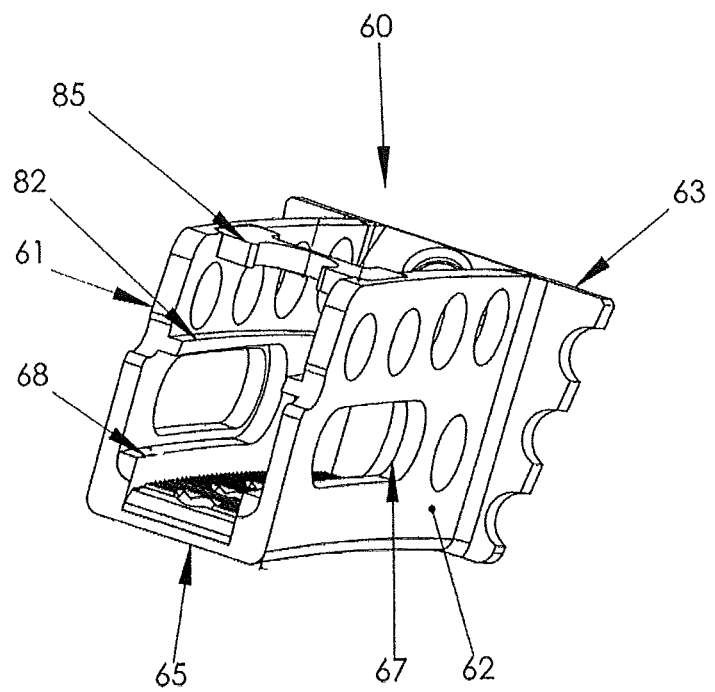
Figure 10:
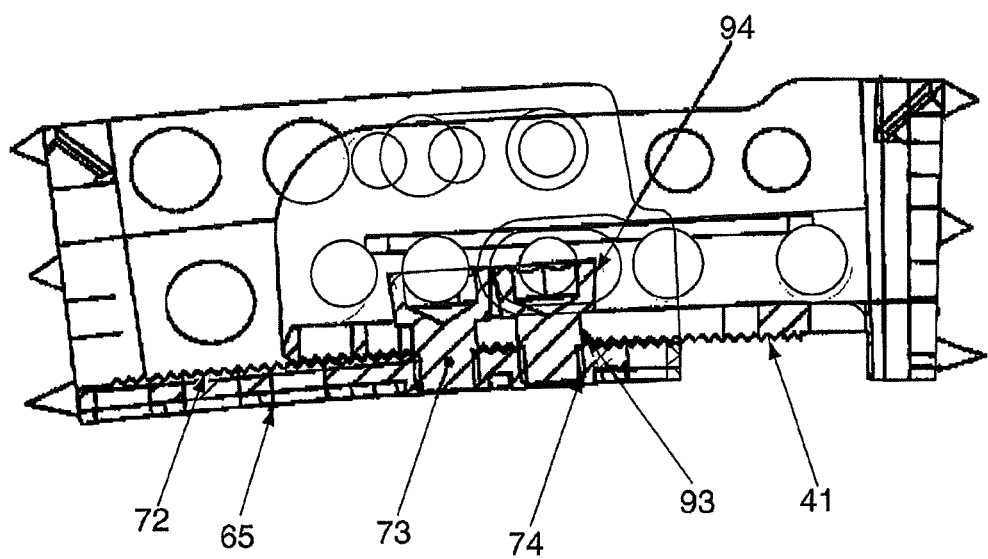
Figure 11:
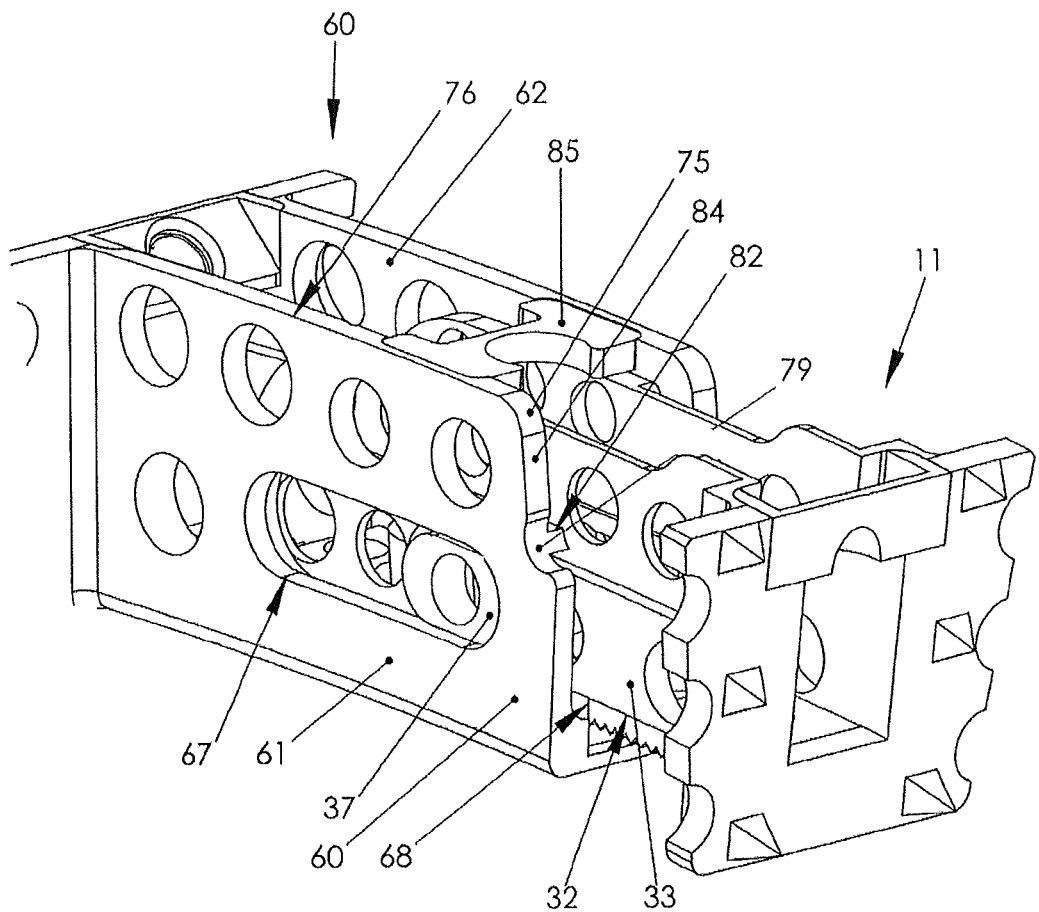
Figure 12:
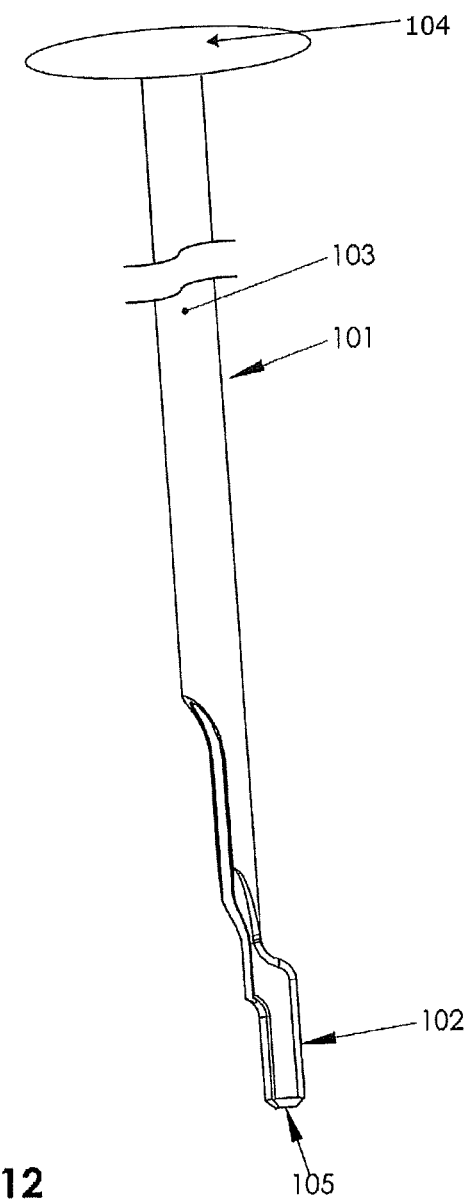
Figure 13:
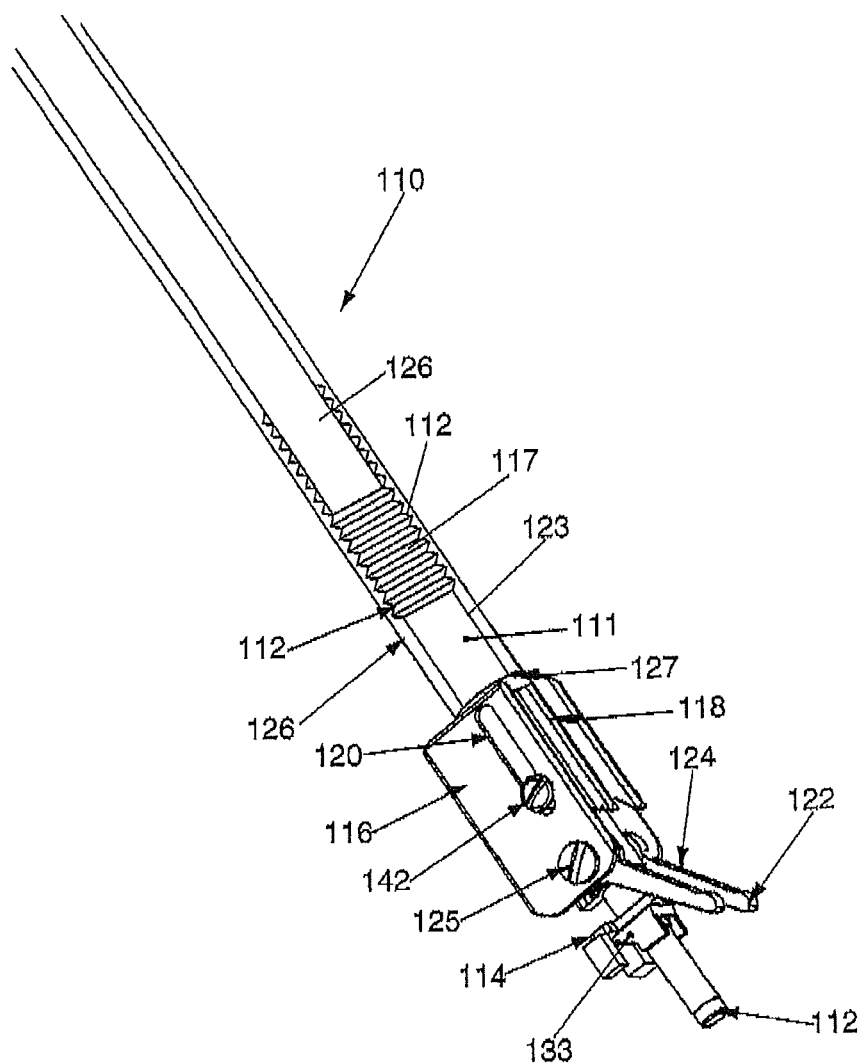

In the figures:

FIG. 1 shows a perspective view of the implant with an inner cage with screw guided in the outer cage, FIG. 2 shows a perspective view of the inner cage, FIG. 3 shows a side view of the inner cage, FIG. 4 shows a plan view of the inner cage from below, FIG. 5 shows a plan view of the end face of the inner cage, FIG. 6 shows a perspective view of the outer cage, FIG. 7 shows a perspective view of the outer cage obliquely from below, FIG. 8 shows a plan view of the outer cage from above, FIG. 9 shows a plan view of the long side of the limbs of the outer cage, FIG. 10 shows a section through FIG. 1 along line A-A, with screws, FIG. 11 shows a perspective view of the end face of the inner cage of the implant, FIG. 12 shows a side view of the retainer, FIG. 13 shows a perspective view of the actuating instrument in the expansion position with actuating sleeve, FIG. 14 shows a plan view of the positioning disk from below, FIG. 15 shows a side view of the actuating instrument in the expansion position, without housing, FIG. 16 shows an overall view of the actuating instrument in the rest position, FIG. 17 shows the implant with actuating instrument in the rest position, FIG. 18 shows the implant with actuating instrument in the expansion position.

The implant shown in FIG. 1 comprises an inner cage 11 and an outer cage 60, the cages 11, 16 are U-shaped, and the inner cage 11 is embraced by the outer cage 60 and is telescopically guided in this cage 60. Both cages 11, 60 are equally aligned, i.e. the limbs 61, 62, 12, 13 of the two cages and also the bottoms 16, 65 of the two cages 11, 60 adjoin each other in the starting position, i.e. the implant is likewise U-shaped.

In the starting or rest position, i.e. the inner cage 11 is pushed completely into the outer cage 60 (cf. also FIG. 17), the side edge 78 of the limbs 61, 62 of the outer cage bears on the inwardly facing side 15 of the vertebral support surface 18 of the inner cage 11, and the outer cage 60 completely embraces the inner cage except for the end face 18 thereof.

The inner cage 11 (FIGS. 2-5) has two limbs 12, 13 with circular passages or recesses 34, 35, 36. The passages 34, 35, 36 permit better through-growth of bone. Corresponding recesses and passages 64 are also located in the limbs 61, 62 of the outer cage 60.

The implant is mirror-symmetrical with respect to the plane (xL plane) in the direction of the longitudinal axis L.

The bottom side 16 of the inner cage 11 connects the two limbs 12, 13 and has an oblong hole 17 that extends in the longitudinal direction L of the inner cage 11. The two edges 14 of the oblong hole 17 run parallel to each other. This oblong hole 17 allows an adjustment position to be secured or temporarily fixed by means of a fastening screw 73 (FIG. 1, FIG. 10).

Between the oblong hole 17 and the end face 18 of the inner cage 11 (cf. FIG. 4), a further bore 26 is provided in the bottom side 16 of the inner cage 11 and serves for the engagement of the actuating instrument 110. The bore 26 comprises a thread, such that the fixation rod 111 of the actuating instrument 110 can be screwed with the outer thread 112 into the bore 26 and, in this way, the actuating instrument 110 can be rigidly connected to the inner cage 11 (FIG. 18).

On the side of the oblong hole 17 opposite this bore 26, a further bore 27 is provided in the underside 16 of the inner cage 11.

During or after insertion of the implant, the openings or bores 17, 27 in the bottom 16 serve for visually monitoring the spinal canal or the dura. This increases the safety of implantation and lessens the radiation burden by reducing the number of X-ray controls that are needed.

On the end face 18 of the inner cage 11 (FIG. 5), vertebral support surfaces 19 or webs 20 are provided, and, alternating with these support surfaces 19 or webs 20, also tooth-shaped locking projections 24 extending in the longitudinal direction L. The vertebral support surfaces 19 or webs 20 are wider than the end faces of the limbs 12, 13, so as to make available a sufficiently large contact area for the vertebral bodies and permit secure anchoring of the implant on the end plate of the adjacent vertebra. Beveled end plates 21 can be provided on the vertebral support surfaces 19 and have bores 22 through which the inner cage 11, if so desired, can be screwed onto the vertebral bodies.

Between the vertebral support surfaces 19 and the web 20, there is an opening 23 (FIG. 5) that permits better through-growth of bone.

At their tips, the locking projections 24 on the respective vertebral support surfaces 19 can have a ground surface 25 for surface penetration and for optimal anchoring on the respectively opposite end plate of the adjacent vertebral body.

The end face 63 and vertebral support surface 70 of the outer cage 60 is designed in accordance with the end face 18 of the inner cage 11.

The end faces 18, 63 of the cages 11, 60 extend transversely with respect to the longitudinal direction L, i.e. with respect to the direction of movement of the cages 11, 16.

On the outsides of each of the limbs 12, 13 of the inner cage 11, a projecting portion 33 is provided which comprises the round openings 34, 35 that allow bone to grow in.

The upwardly directed face 50 of the portion 33 forms a guide for the two lever ends 122 of the screwed-in instrument 110. Upon actuation of the instrument 110, the sliding elements or lever ends 122 are guided along the edge 50 in the L direction and moved by the movement of the lever ends/ sliding elements 122 in the L direction of the outer cage 60. The guide edge 50 likewise has the lordotic shape deviating slightly from the straight.

The portion 33 comprises a further projection 37, of which the external diameter 38 in the X direction is slightly smaller than the internal diameter 66 of the corresponding oblong hole 67 in the limbs 61, 62 of the outer cage 60. The projection 37 is guided in the oblong hole 67 and limits the displaceability of the inner cage 11 relative to the outer cage in the L direction and prevents displacement of the cages relative to each other in the X direction. The opening 34 can also be provided in the guide projection 37, which can have an approximately oval shape.

On the outside of the limbs 12, 13 of the inner cage 11, a further projection 40 is provided in the upper area, at the end opposite the end face 18. The lower edge 43 of the projection 40 likewise has a slight curvature following the lordotic shape and is guided, at a corresponding edge 82 (FIG. 9), on the inside of the limbs 61, 62 of the outer cage 60. In the area of the projections 40, circular openings 36 can likewise be provided that allow bone to grow through.

In the area near the bottom of the outwardly facing sides of the limbs 12, 13, the lower edge 32 of the projection 33 extends in the longitudinal direction and serves to guide a corresponding rail 68 in the inwardly facing corner area near the bottom of the outer cage 60 (FIG. 9, FIG. 11).

The annular projection 37 and oblong hole 67, the lower edge 43 of the projection 40 and the guide edge 82, edge 92 and rail 68 are corresponding guide elements which are provided on the outer cage 60 and inner cage 11 and which all extend in the L direction in a form deviating slightly from a straight line. They serve to ensure that the inner cage 11 can be moved relative to the outer cage 60 in a line of slight curvature corresponding to the lordotic shape, e.g. of the cervical spine, without jamming.

At the face lying opposite the front face 18 of the inner cage 11, the end area of the limbs 12, 13 in the L direction merges in the shape of an arc 44 into the top face 42 of the limbs 12, 13, so that the implant can be fully closed.

On the top face 42 of the limbs, near the front face 18, the top face 42 of the limbs rises to attain the height of the front face 18, such that the top face 46 of the limb 12, 13 near the front face and the top face 47 of the front area form a continuous bearing surface for the positioning disk 114 of the instrument 110.

On the underside of the bottom 16 of the inner cage 11, in the area of the oblong hole 17, a toothing 41 is provided which serves for better fixing of the inner cage 11 relative to the outer cage 60 by providing additional locking after screwing has been completed.

At the front face 63, the outer cage 60 (FIGS. 6, 7, 8) is designed in accordance with the front face 18 of the inner cage 11 and has vertebral support surfaces 70, which correspond to the vertebral support surfaces 19 described in the inner cage 11.

The bottom 65 of the outer cage 60 likewise comprises several bores or passages 71 that serve for better through-growth of bone and for visual monitoring during implantation. On the top face of the bottom 65, teeth 72 are provided that serve for engagement in the corresponding teeth 41 on the outside of the bottom 16 of the inner cage 11.

In the bottom 65 of the outer cage 60, screws 73 are moreover provided in the threaded bore 74 of the outer cage 60 (FIGS. 7 and 10), wherein the screw shank 93 is guided through the oblong hole 17 in the bottom of the inner cage 11, and the screw head 94 bears on the top face of the bottom 16 of the inner cage 11. When the screw 73 is loosened, the inner cage 11 is movable relative to the outer cage 60. When the screw 73 is tightened, the teeth 41, 72 engage in one another and the expansion position is fixed. The fixing screw is secured against falling out.

The length of the screw shank 93 and the size of the bore 74 are dimensioned such that, even when the screw 73 is tightened in the bore 74, the end of the screw does not protrude beyond the underside of the bottom 65 of the outer cage 60.

The underside of the bottom 65 of the outer cage is flat, except for the slightly lordotic curvature, and does not have the wall thickness that is known from the prior and that can lead to complications.

Depending on the size of the implant, the number of screws 73 and bores 764 can also be increased to two or more.

The two limbs 61, 62 of the outer cage 60 likewise have openings 64 that serve for better through-growth of bone, and the already described oblong hole 67 which, together with the projection 37 in the inner cage 11, serves for guiding purposes. The two mutually parallel long sides of the oblong hole 67 do not extend completely in a straight line but are instead slightly curved, following the lordotic shape.

On the face opposite the front face 63, the side edge 78 of the limbs 61, 62 of the outer cage 60 merges in the L direction, in the form of an arc 75, into the top face 76 of the limbs 61, 62. The side edge 78 of the limbs 61, 62 has a step 79 which, in an arc of a circle with the radius r, merges into the slightly beveled upper area 84 of the side edge 78.

The step 79 serves to support the lever ends/sliding elements 122 of the actuating instrument.

On the top face 76 of the limbs 61, 62, a web 85 is also provided which bridges the open side 80 of the implant and is connected to both webs 61, 62.

The web 85 serves as a bearing for the instruments, such as a screwdriver, or the retainer 101 described below.

For this purpose, the web 85 has recesses 86, 87 on both sides, which recesses serve to receive these instruments. The U-shaped recess 86 serves for the positioning of a correspondingly shaped retainer 101 (rotation retainer) which, when the screws are screwed in, serves to take up the torque and thus prevents the torque being transferred to the implant.

The retainer 101 (FIG. 12) comprises a bar 103 with handle 104 and, in the lower area, a rectangular bar shape corresponding to the recess 86 in the web 85, such that the retainer 101 can bear with its outer wall 102 in the end area on the outer surfaces of the U-shaped recess 86 in the web 85.

The circular recess 87 in the web 85 accordingly serves as a guide for a screwdriver or hexagon wrench. The top face 42 of the limbs of the inner cage 11 extends underneath the bridging web 85, the underside of the bridging web 85 forms a further guide.

The outer cage 60 and inner cage 11 can be filled with bone chips or bone substitute material via the open side 80 (i.e.

from +direction). Osseous union with the adjacent vertebrae is possible through the opening 23 in the vertebral support surfaces 19, 70 and the openings 34, 35, 36, 64, 71, 67.

The open side 80 lies opposite the bottoms 16, 65 of the two cages 11, 60.

The outer cage 60 and inner cage 11 form a captive unit.

For expansion of the two cages 11, 60, an actuating instrument 110 (FIG. 13) is used which comprises the rigid fixation rod 111 and the expansion mechanism, which causes a pivoting movement of the lever ends 124 that form the sliding elements 122. At the lower end of the guide rod 111, an outer thread 112 is provided which, by a rotation movement of the guide rod 111, can be screwed into the thread of the bore 26 in the bottom 16 of the inner cage 11.

Above the thread 112, approximately at a height corresponding to the height of the inner cage 11, a positioning disk 114 (FIGS. 13 and 14) is provided on the fixation rod 111, the contour of which positioning disk 114 corresponds approximately to the plan view of the open side 80 in the front area of the inner cage 11, which likewise is approximately T-shaped. When the guide rod 111 is inserted from above into the open side 80 of the inner cage 11 and screwed tight, the underside of the positioning disk 114 bears on the top faces 46 of the limbs 12, 13 and on the top face 47 of the front area. On one side 133 of the approximately T-shaped positioning disk 114 (FIGS. 13 and 14), a semicircular recess 134 is again provided for receiving the fixation rod 111.

The positioning disk 114 is secured rotatably but non-displaceably on the fixation rod 111. The lever ends 122 of the instrument 110 are guided along the side edges 131 of the T-shaped positioning disk 114.

In this way, the positioning disk 114, the lever ends/sliding element 122 and the entire expansion mechanism connected to the lever ends/sliding element 122 are positioned relative to one another and permit the rotation movement of the rod 111 relative to these elements surrounding the rod 111, to the expansion mechanism and to the positioning disk 114 connected to the expansion mechanism via the rod 111 and bore 130.

The expansion mechanism, which is movable on the bar 111, is provided above the positioning disk 114. The path of movement is limited by the positioning disk 114 and the threaded spindle 117.

The expansion mechanism comprises a force transmission element 118 which, in the lower side area, has an oblique pressing surface 119. The expansion mechanism further comprises a guide pin 142 which passes through the force transmission element 118 and which is forcibly guided in an oblong hole 120 extending parallel to the rod 111. The oblong hole 120 is located in a U-shaped housing 116 surrounding the force transmission element 118. At the lower end of the housing 116, the lever elements 124 are provided which are mounted rotatably about the axis 125. The upper ends 128 of the lever elements 124 are beveled.

In the rest position, there is no force acting on the force transmission element 118, the guide pin 142 is located at the upper end of the oblong hole 120, and the upper end 128 of the lever elements 124 bears on the bevel 119 in the rest position (FIGS. 16 and 17). Lever elements 124 and lever ends/sliding elements 122 extend downward substantially parallel to the rod 111. For this purpose, a spring element is provided that holds the lever ends 122 in the rest position.

If the force transmission element 118 is now pushed down along the rod 111 (FIG. 15, FIG. 18 (arrow B)), the beveled pressing surface 19 presses onto the upper lever end 128, such that the lower end 122 of the lever element 124 is pivoted outward relative to the rest position.

In this displacement movement of the force transmission element 118, the latter is forcibly guided in the oblong hole 120 in the U-shaped housing 116. As a result of this displacement movement, the lever ends/sliding elements 122 move on a circular trajectory.

Since the lever ends/sliding elements 122, in the rest position in the step 79, bear on the side edge 78 of the outer cage 60 (FIG. 17), the pivoting movement of the lever end 122 of the instrument 110 on the circular trajectory, and the guiding along the upper edge 50 of the portion 33 in the inner cage 11, leads to a displacement of the outer cage.

A precisely defined displacement movement of the force transmission element 118 along the guide rod 111 screwed onto the inner cage 11 can be achieved by a sleeve-shaped actuating element 123 which, near the lower end, has an inner thread 126 corresponding to the threaded spindle 117 on the guide bar 111.

By means of the metered screwing of the inner thread 126 onto the threaded spindle 117, the lower edge 127 of the actuating sleeve 123 gradually moves downward and, as a result of this movement, presses on the force transmission element 118, as a result of whose displacement the lever ends 122 are deflected and the outer cage is thus displaced relative to the inner cage 11, which is rigidly connected to the fixation bar 111.

All of the elements provided at the lower end of the instrument 110 are designed in such a way that the slender shape of the guide rod 111 is substantially maintained and, therefore, no bulky devices are provided that obstruct the operating field.

A further advantage of the instrument 110 is that it is secured in the inner cage 11 near the front face 18 of the inner cage 11 and, as a result, the view of the operating area is obstructed as little as possible by the instrument 110.

As a result of the slender configuration of the operating parts, the space-saving rotation movement of the sleeve 123 for actuating the expansion mechanism, the placement of the instrument in such a way that there is no contact with the valves, it is possible for the entire surgical incision to be made smaller than is the case in previously known corpectomy cages.

Another important advantage of the present invention is that improved X-ray monitoring can take place during the implantation, since the view is only slightly impaired by the slender instrument 110, this being an important difference from the large, forceps-like operating elements previously known.

The instrument 110 according to the invention is based on a separation of the functions of "fixating" and "expansion". The instrument 110 or fixation rod 111 is fixed initially by securing the outer thread 112 at the end of the guide rod 111 in the threaded bore 26. It is only when the guide rod 111 has been screwed firmly into the threaded bore 26 that the sleeve-shaped actuating element 123 is screwed onto the threaded spindle 117 and, in this way, the pivoting mechanism on the lever ends 122 activated.

During the displacement of the outer cage 60 relative to the inner cage 11, the guide rod 111 is prevented from slipping out, since the rotation movement on the actuating sleeve 123 is decoupled from the rotation movement on the outer thread 112 in the guide rod.

By "unscrewing" the actuating sleeve 123, the force transmission element 118 is pivoted upward again and the lever ends 122 are once again pivoted in the direction of the rest position such that, with this implant 10 and this instrument 110, an easily controllable, reliably functioning overexpansion of the cages can be reversed again.

The screwdriver used is preferably a hexagon wrench since the slender shape thereof once again barely obstructs the view of the operating field at all.

The openings provided in the outer cage 60 and inner cage 11 in the limbs 12, 13, 61, 62 also permit monitoring of the fit of the implant, which can be monitored by lateral X-ray.

Moreover, as a result of the lordotic shape of the corpectomy cage according to the invention, no additional implant is needed any longer.

By means of the instrument 110 according to the invention and the implant 10 according to the invention, an expansion movement is permitted that follows the lordotic shape of the corpectomy cage, without the two cages jamming against each other during the expansion procedure.

Controllability can additionally be improved by the fact that the inner cage 11 and housing 116 of the instrument 110 are marked with colors, such that the correct orientation of the instrument 110 relative to the implant is also assisted by colors.

The corpectomy cage according to the invention is additionally characterized in that optimal bone formation can be achieved and, in the event of overexpansion, the position can be easily reversed again.

The invention claimed is:

1. An implant device comprising; an actuating instrument and a height-adjustable implant, the height-adjustable implant comprising an inner cage and an outer cage, wherein the inner cage is substantially U-shaped in cross-section, wherein the inner cage comprises a bottom, a front face, and limbs, wherein the outer cage is U-shaped in cross-section, wherein the outer cage comprises a bottom, a front face, and limbs, wherein the inner cage of the implant is received by the outer cage and telescopically guided, and the inner cage and the outer cage are equally aligned, and wherein the limbs of the inner cage and the limbs of the outer cage are aligned such that a substantially continuous lateral opening lies opposite the bottoms of the two cages, and the inner and outer cages can be fixed with respect to each other in a predetermined end position, and wherein vertebral support surfaces are provided on the front faces of the cages, characterized in that the actuating instrument has a fixation rod and an expansion mechanism with sliding elements, and the inner cage and the fixation rod have corresponding elements, by means of which a releasable, rigid connection between the fixation rod and the inner cage is achieved, and wherein, by actuating the expansion mechanism on the actuating instrument, the outer cage can be moved in a longitudinal direction relative to the inner cage by engagement of the sliding elements on the limbs.

2. The implant device as claimed in claim 1, characterized in that one of the corresponding elements is a bore with thread in the bottom of the inner cage.

3. The implant device as claimed in claim 1, characterized in that one of the corresponding elements is an outer thread on the fixation rod.

4. The implant device as claimed in claim 1, characterized in that the limbs of the inner cage have outsides and that, on the outsides of the limbs of the inner cage, a support surface is provided which extends in the longitudinal direction and on which the sliding elements are supported during actuation of the expansion mechanism of the actuating instrument.

5. The implant device as claimed in claim 1, characterized in that the limbs of the outer cage have a side that lies opposite the front face of the outer cage and that, on the side of the limbs that lies opposite the front face of the outer cage, a step is provided which serves to support ends of the sliding elements of the actuating instrument.

6. The implant device as claimed in claim 1, characterized in that the outer cage has a bridging web which bridges the lateral opening and which is rigidly connected to the limbs and comprises recesses for receiving instruments.

7. The implant device as claimed in claim 1, characterized in that corresponding elements are provided on the limbs of the cages and serve to guide movement of the two cages in a movement that follows a lordotic shape.

8. The implant device as claimed in claim 7, characterized in that the corresponding elements are corresponding support surfaces or openings with projections guided into the openings.

9. The implant device as claimed in claim 8, characterized in that the corresponding support surfaces or openings with projections are in a form slightly deviating from straight.

10. The implant device as claimed in claim 1, characterized in that the inner cage has an oblong hole in the bottom and the outer cage has openings in the bottom, and a screw connects the cages through the openings.

11. The implant device as claimed in claim 1, characterized in that the limbs have openings and/or the bottoms have openings and/or the vertebral support surfaces have openings, which allow bone to grow through.

12. The implant device as claimed in claim 1, characterized in that the fixation rod comprises a rod end, the rod end being provided with an outer thread.

13. The implant device as claimed in claim 1, characterized in that the sliding elements and the expansion mechanism are provided near an end of the fixation rod.

14. The implant device as claimed in claim 1, characterized in that the expansion mechanism comprises a force transmission element with an oblique pressing surface and lever elements, the lever elements comprising the sliding elements and being mounted pivotably about an axis, wherein the lever elements comprise upper ends that bear on the pressing surface in a rest state, and, when force is introduced by pressure on the oblique pressing surface of the force transmission element, the sliding elements are pivoted out of a rest position.

15. The implant device as claimed in claim 14, characterized in that the force transmission element is surrounded by a U-shaped housing with an oblong hole, and a guide pin is provided that passes through the force transmission element and is forcibly guided in the oblong hole.

16. The implant device as claimed in claim 15, characterized in that the housing comprises a lower end, the lower end of the housing passing through an axis on which the lever elements are secured pivotably.

17. The implant device as claimed in claim 1, characterized in that the expansion mechanism is displaceable relative to the fixation rod.

18. The implant device as claimed in claim 1, characterized in that the fixation rod has a threaded spindle, the threaded spindle comprising an outer thread on which an actuating sleeve can be screwed, and wherein, by screwing, a lower edge of the actuating sleeve presses a force transmission element downward toward an end of the fixation rod.

19. The implant device as claimed in claim 1, characterized in that the fixation rod has a fixation disk which is mounted so as to be rotatable near an end of the fixation rod but not displaceable from the fixation rod.

20. The implant device as claimed in claim 19, characterized in that the fixation rod has a threaded spindle and that a displacement path of the expansion mechanism along the fixation rod is limited by the fixation disk and the threaded spindle.

21. The implant device as claimed in claim 19, characterized in that the expansion mechanism, together with the fixation disk, is rotatable relative to the fixation rod.

22. The implant device as claimed in claim 19, characterized in that the expansion mechanism is not rotatable relative to the fixation disk.

23. The implant device as claimed in claim 1, characterized in that the outer cage comprises a bridging web, the bridging web comprising a recess, and characterized in that a retainer is also provided, wherein the retainer can be positioned on the recess on the bridging web.

* * * * *